United States Patent
Bain et al.

(10) Patent No.: US 6,631,288 B1
(45) Date of Patent: Oct. 7, 2003

(54) SKIN EVALUATION APPARATUS

(75) Inventors: Duncan Shirreffs Bain, Hertfordshire (GB); Martin William Ferguson-Pell, Chesham Bois (GB); Alastair George Mcleod, Rugby (GB)

(73) Assignee: Huntleigh Technology, PLC (GB)

( * ) Notice: Subject to any disclaimer, the term of this patent is extended or adjusted under 35 U.S.C. 154(b) by 0 days.

(21) Appl. No.: 09/701,994

(22) PCT Filed: Apr. 5, 2000

(86) PCT No.: PCT/GB00/01280
§ 371 (c)(1),
(2), (4) Date: Dec. 6, 2000

(87) PCT Pub. No.: WO00/60349
PCT Pub. Date: Oct. 12, 2000

(30) Foreign Application Priority Data

Apr. 6, 1999 (GB) ............................................. 9907613

(51) Int. Cl.⁷ ............................................. G01N 33/483
(52) U.S. Cl. ....................................... 600/476; 600/477
(58) Field of Search ................................. 600/476, 477

(56) References Cited

U.S. PATENT DOCUMENTS 5,054,502 A * 10/1991 Courage ..................... 600/476
5,372,135 A    12/1994 Mendelson et al.

OTHER PUBLICATIONS

PCT Search report, EPO, Dec. 22, 2000.*
Utz et al.: "Flourescence spectroscopy in combination with reflectance measurements in human skin examination; what for and how?", Jan., 1995, Proc. Spie, Optical Biopsy And Flourescence Spectroscopy and Imaging, vol. 2324, Cubeddu, Marchesini, Mordon, Svanberg, Rinnebarg, Wagneires, Eds. XP002156301.

Database Medline Online! STN AN–94308989, Oct. 1994 XP002156302.
Hasigawa et al.: "Assessment of skin blood content and oxygenation in spinal cord injured subjects during reactive hyperemia", Journal Of Rehabilitation, Research and Development, vol. 31, No. 1, 1994, pp. 1–14.
Database Medline Online! STN AN–90318934, Oct. 1990 XP002156303.
Anderson, et al.: Spectral reflectance of human skin in vivo, Photodermatology, Photoimmunology and Photomedicine, vol. 7, No. 1, 1990, pp. 5–12.
Meijer J.H. et al., "Method For The Measurement Of Susceptibility To Decubitus Ulcer Formation", medical and Biological Engineering and Computing, GB, Peter Peregrinus LTd. Stevenage, vol. 27, No. 5, Sep. 1, 1989 pp. 502–506, XP 000046404.

* cited by examiner

Primary Examiner—Michael-Powell Buiz
Assistant Examiner—Ramesh Krishnamurthy
(74) Attorney, Agent, or Firm—Brown Raysman Millstein Felder & Steiner LLP

(57) ABSTRACT

A skin evaluation apparatus and method for rapidly assessing the degree of erythema of the skin and the skin's response to blanching. The apparatus includes a housing comprising a probe head having an emitter and sensor and a blanching edge. The emitter consists of bundles of optical fibers by means of which light from LEDs is delivered to and recovered from the skin. In use, the probe head is held flush with the skin surface causing the blanching edge to indent a fixed area of skin causing a local blanche. As the probe head is moved, the blanching edge slides along the skin surface evacuating blood as it moves. During the blanche, the LEDs are switched on and the scattered signal collected using a photodiode. A processor measures the attenuation of scattered light and gives a display of blood content against time, providing an indication of the blood circulation in that area.

19 Claims, 5 Drawing Sheets

SKIN EVALUATION APPARATUS

BACKGROUND OF THE INVENTION

1. Field of the Invention

The present invention relates to a tissue evaluation apparatus and method for rapidly assessing non-invasively the tissue status particularly with respect to the quality of microcirculation, susceptibility to mechanical force related damage and differentiation of bruised or necrotic dermal or sub-dermal tissue from that which is healthy or erythemous.

The apparatus and method of the present invention is particularly effective in, but not limited to, the early detection of a pressure ulcer. Any medical condition or disease which can be assessed by measuring the competence of microcirculatory supply and drainage will also be a potential application for this technique.

2. Discussion of Related Art

The first sign of a pressure ulcer is as an area of persistent redness which may be visible on some skins and not others depending upon their pigmentation. This persistent redness is due to soft tissue being compressed for a long period of time between a bone and a firm surface such as a mattress causing an interruption of the blood supply which the body corrects by means of a temporary elevation of the blood flow to the area.

Clinically, nurses are able to detect early pressure ulcers by the redness of the skin by compression of a reddened area with a finger to 'blanche' the area and assessing the rate at which the blanche disappears. If the reddened area of skin blanches and then returns to red on release of pressure within a predetermined time, this is called blanchable erythema, and is not generally considered to constitute a serious change in skin health by nurses.

In cases where the redness or erythema persists after compression with a finger, called non-blanchable erythema, this is an indication that damage has occurred, due to a more severe interruption of the blood supply and inflammation, either due to excessive pressure or lower pressures acting over a longer duration, bringing about a more serious change in the blood circulation.

The 'finger blanche' test is problematic in that it requires much subjective judgment on the part of the nurse or clinician, and the variances of skin pigmentation and condition make it difficult to observe changes over time. An existing laboratory based technique has been described to monitor and characterise skin redness using tissue reflectance spectroscopy (TRS). A fibre optic probe is used to deliver light and detect back-scattered light from the superficial dermis. The back-scattered light can be analysed for spectral components that have interacted with the blood. Using appropriate analysis algorithms it is possible to determine indices of blood content and oxygenation for the superficial skin vasculature.

Although these procedures allow precise and reliable measurements, their current use is limited to static measurement of quantities related to blood content in the skin. This does not necessarily relate to the seriousness of damage, which is established using manual methods by expelling blood from an area and observing the speed of re-colouration using the human eye. This dynamic measurement of the skin's response to blanching, is a more accurate indication of the degree of damage caused to the microcirculatory system, because the damaged area contains a higher degree of extravascular blood than an undamaged area.

Response to blanching has been identified as having value both in identifying erythema, and in differentiating between different types of erythema: non-blanching erythema exhibits a fast recovery of blood content after blanching, whereas reactive hyperemia (blanching erythema) exhibits a slow response.

SUMMARY OF THE INVENTION

The apparatus and method of the present invention may also be applied to dermal and/or sub-dermal tissues, or any internal or external tissue surface whether of human or other mammals and whether natural or created artificially by way or surgery or injury.

An object of the present invention is to provide a rapid and non-invasive diagnostic apparatus and method for assessing and differentiating damage to tissue microcirculation, for instance non-blanching and blanching erythema of the skin, by the measurement of blood content and the response of tissue to blanching. The method of analysis makes the determination of this damage insensitive to any tissue pigmentation which may be present. The method and apparatus of the invention overcomes the limitation of current human eye analysis by manipulating the reflectance data to subtract the effect of skin pigment (melanin).

A further object of the present invention is to predict the susceptibility of undamaged tissue to ulceration should adverse circumstances arise and also to predict the likelihood of further deterioration in skin condition in patients exhibiting blanching erythema (based on a library of information derived in extensive clinical trials)

Additionally, the present invention can be used to differentiate bruised or necrotic dermal or sub-dermal tissue from healthy or erythemous tissue by analysing both the level of deoxygenated or oxygenated blood in an area together with the dynamic response using a specially constructed algorithm developed on a neural network system. The apparatus and method of the present invention forces the blood from an area of tissue and monitors the rate of return of the blood back into the area. High blood content is an indication of inflamed tissue (erythema), but the rate at which blood flows back following expulsion is a more powerful indicator of the state of tissue damage, because static colour data alone does not indicate the extent of infarction and obliteration of the microcirculation and therefore the likelihood of the skin breaking down further under continued pressure.

The same technique can also be used on non-damaged tissue to assess the likelihood of the development of pressure ulcers. The blanching response of suspect tissue may be compared with information derived during clinical trials and characterised using neural network techniques. Thus, "high risk" tissue can be identified, and it is possible to take the appropriate steps to prevent further damage, for instance pressure ulcers.

For patients assessed to be at high risk according to the apparatus and methods herein described, that a pressure ulcer may be forming, the patient could be moved to a support surface providing pressure reduction or pressure relief on the body. The patient can be monitored more closely (and re-assessed using the instrument and methods described) to make sure that pressure on particular vulnerable areas is avoided.

Therefore, the present invention can be used to reduce the development of pressure ulcers, as well as the early detection of any incipient pressure ulcers or the susceptibility of the tissue to microcirculatory damage.

According to one aspect of the present invention, an apparatus is provided for evaluating microcirculatory status or damage adjacent the tissue surface comprising a means for applying a mechanical stimulus to an area of the tissue surface, means for delivering light to said area of tissue and one or more sensors for detecting the light recovered from the tissue, a processor means connected to the sensor(s) and delivery means for determining the attenuation of different wavelengths of light scattered within the tissue to provide an indication of the state of the microcirculation of said area of tissue. The blood content value against time is determined to provide an indication of the quantity and mobility of extra-vascular blood in said area of tissue Preferably, the means for applying a mechanical stimulus comprises applying a pressure and more preferably comprises a housing having a blanching edge to apply a sliding force on the body surface to provide a blanching effect. Advantageously, the sliding blanche has the capacity to produce a very even and complete blanche, without the requirement for exact control of the applied pressure.

Preferably, the means for delivering light is a transmitter which may be located remote from the housing or optionally may be located within the housing for a more compact diagnostic apparatus. Preferably the sensor(s) may be located adjacent the edge within the housing for more accurate measurements.

It will be understood that light can include the range of electromagnetic radiation wavelength comprising both the visible and near visible spectrum. Also the choice of transmitter wavelength or frequency distribution, receiver sensitivity, relative transmitter and receiver geometry, and interpretation of the variation of scattering attenuation of light within the tissue surface and sub-surface layers with time before, during and after mechanical stimulus information of value for diagnosing status risk and predicting progression of other clinical conditions may be produced.

These conditions include diabetes, vascular insufficiency, leg ulcers as well as monitoring status of tissue flaps and skin grafts.

Preferably, the sliding action of the edge necessary to blanche may be powered to avoid inconsistencies that may arise during manual repetitive blanching. Preferably, the blanching edge may have rotary or linear movement, and there may comprise relative motion between the blanching edge and the receiver(s). Preferably, the movement of the blanching edge is at a controlled rate to give a known time interval between the blanching edge and the sensor(s). Preferably, the blanching edge may be oblique relative to the direction of motion, to displace blood laterally.

Preferably, the processor means also measures the level and ratio of oxygenated to deoxygenated blood in an area, which allows identification of bruised or necrotic skin areas as distinct from erythema by analysing the time variation of light attenuation data during the blanching process.

According to another aspect of the present invention there is provided a method for evaluating microcirculatory damage adjacent to the tissue surface comprising the steps of applying a pressure to an area of skin surface, exposing said area to light, measuring the attenuation of different wavelengths of the light scattered within the tissue and collected by the sensor or more sensor(s) and computing blood content against time upon removal of the application of pressure.

The shape of the blood recovery signal indicates the state of microcirculation of the tissue using a set of rules derived from clinical trials.

Preferably, the pressure applied is a sliding force on the surface of the tissue. This method of applying pressure (blanching) has the advantage of being in the main a surface effect, causing little perturbation of the deeper structures.

BRIEF DESCRIPTION OF THE DRAWINGS

An embodiment of the present invention is described below, by way of example only, with reference to the accompanying drawings in which.

DETAILED DESCRIPTION OF THE PREFERRED EMBODIMENTS

Figure 1:
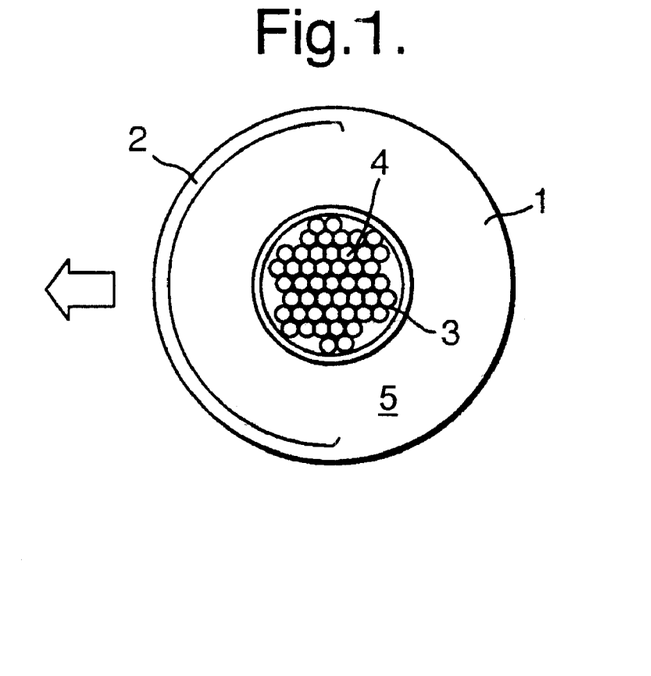
FIG. 1 is a schematic diagram of a probe head according to the present invention.

Referring to FIG. 1, a probe-head (1) comprises an emitter/sensor (3) and a blanching edge (2). The emitter/sensor (3) may consist of one or more bundles of one or more optical fibres (4), by means of which light is delivered to and recovered from the skin. In a preferred embodiment, the emitter/sensor (3) includes LEDs whose range of transmitted wavelength is centered at the 4 wavelength of: 475 nm, 525 nm, 640 nm, 810 nm. Light from each of these 4 LEDs is channeled into one tail of a fibre optic bundle. The four tails join a fifth tail coupled to a photodiode. The other end of the complete bundle forms the emitter/sensor (3).

Figure 2:
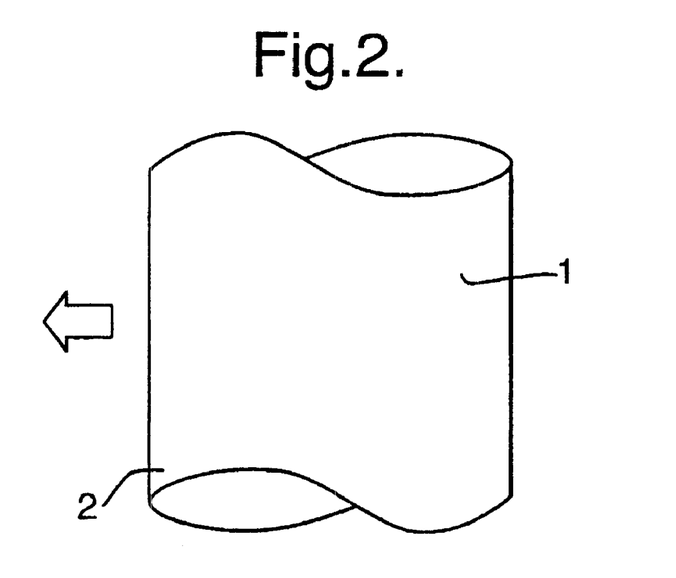
FIG. 2 is a schematic diagram of a side view of FIG. 1.
Figure 3A:
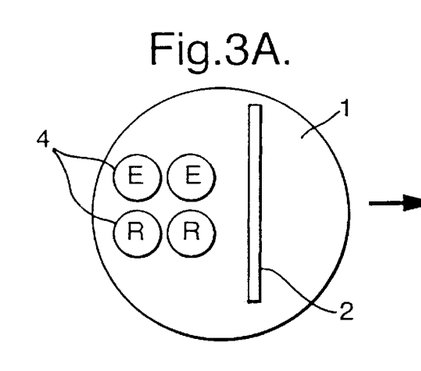
FIGS. 3A to 3E show different combinations of the blanching edge and sensors on the probe head.
Figure 3B:
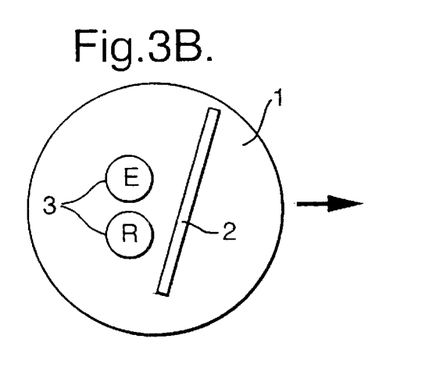
Figure 3C:
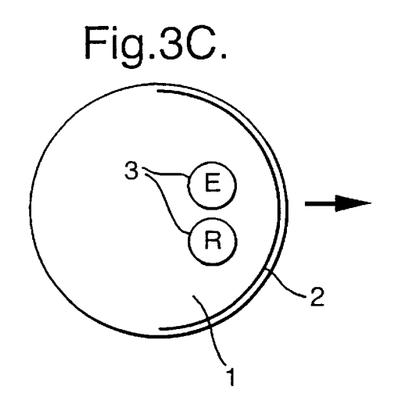
Figure 3D:
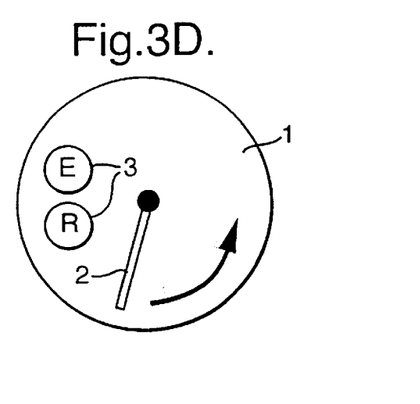
Figure 3E:
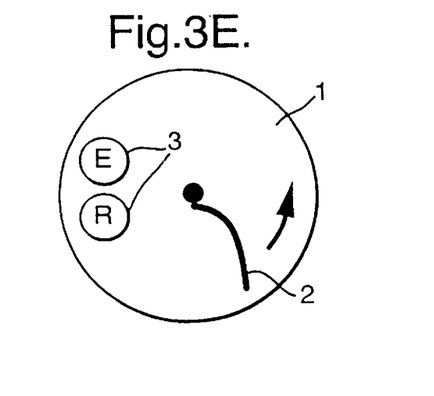

The blanching edge (2) may consist of a portion of the probe-head (1) raised proud of the substantially flat surface (5) that contacts the skin. The flat surface (5) is held flush with the surface of the skin, causing the blanching edge (2) to indent a fixed amount onto the skin, so causing a local blanche. As the probe-head (1) is moved in the direction indicated by the large arrow, the blanching edge (2) slides parallel to the skin surface, while the flat face (5) remains in flush contact with the skin. The blanching edge (2) evacuates blood from the skin as it moves with fixed indentation into the skin, leaving behind it a region of evenly-produced blanche.

After a controlled blanche is produced, the probe-head (1) is brought to a halt. During the blanche, each LED is switched on in turn, and the scattered signal is measured using a photodiode.

The device gives an output of scattered light from the skin at various discrete wavelengths referenced to a pre-calibrated value of light of each respective wavelength scattered from a standard white surface.

Plotted as output against wavelength, these values give a crude absorption spectrum. As well as spectral variation as a result of redness, much variation also exists between subjects as a result of pigmentation and other effects.

Owing to differences in the absorption spectra between blood and melanin, melanin has the effect of increasing absorption across the whole visible spectrum, with only a slightly greater increase at 525 nm than at 640 nm. Blood content, on the other hand, increases absorption much more steeply at 525 nm, and causes little change at 640. This means that although there is crosstalk between melanin and redness at a given wavelength, information of values at 2 or more wavelengths provides means for distinguishing between the two effects. This also yields a rapid method for quantitatively assessing the pigmentation of a skin area if required.

Thus a simple index of blood content, independent of skin pigmentation can be calculated as:

BLOOD=(absorption of LED centered at 525 nm) (absorption of LED centered at 640 nm), which is calculated by the processor and presented as a plot of blood content against time. (The neural net may use a plethora of different indices to relate the blanching trace it is seeing to its library of previously performed traces with known pathologies. As will be appreciated by those skilled in the art, this is only one example of a formula useful for determining blood content by comparing the absorption or reflectance of light or other electromagnetic energy at various frequencies or wavelengths, and is not the only formula useful for doing so.)

Figure 4A:
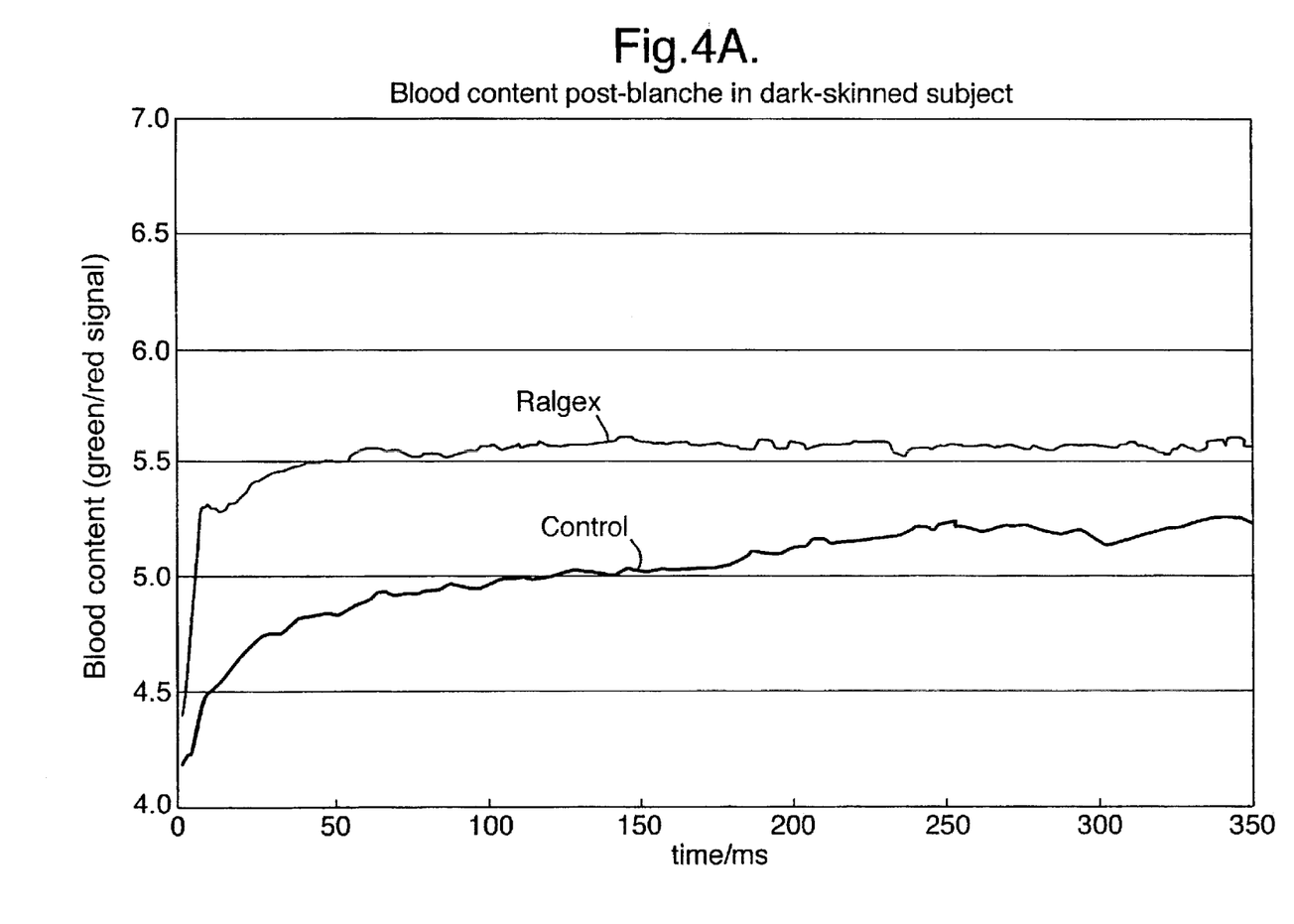
FIGS. 4A and 4B are graphs showing the response to blanching as blood content against time.
Figure 4B:
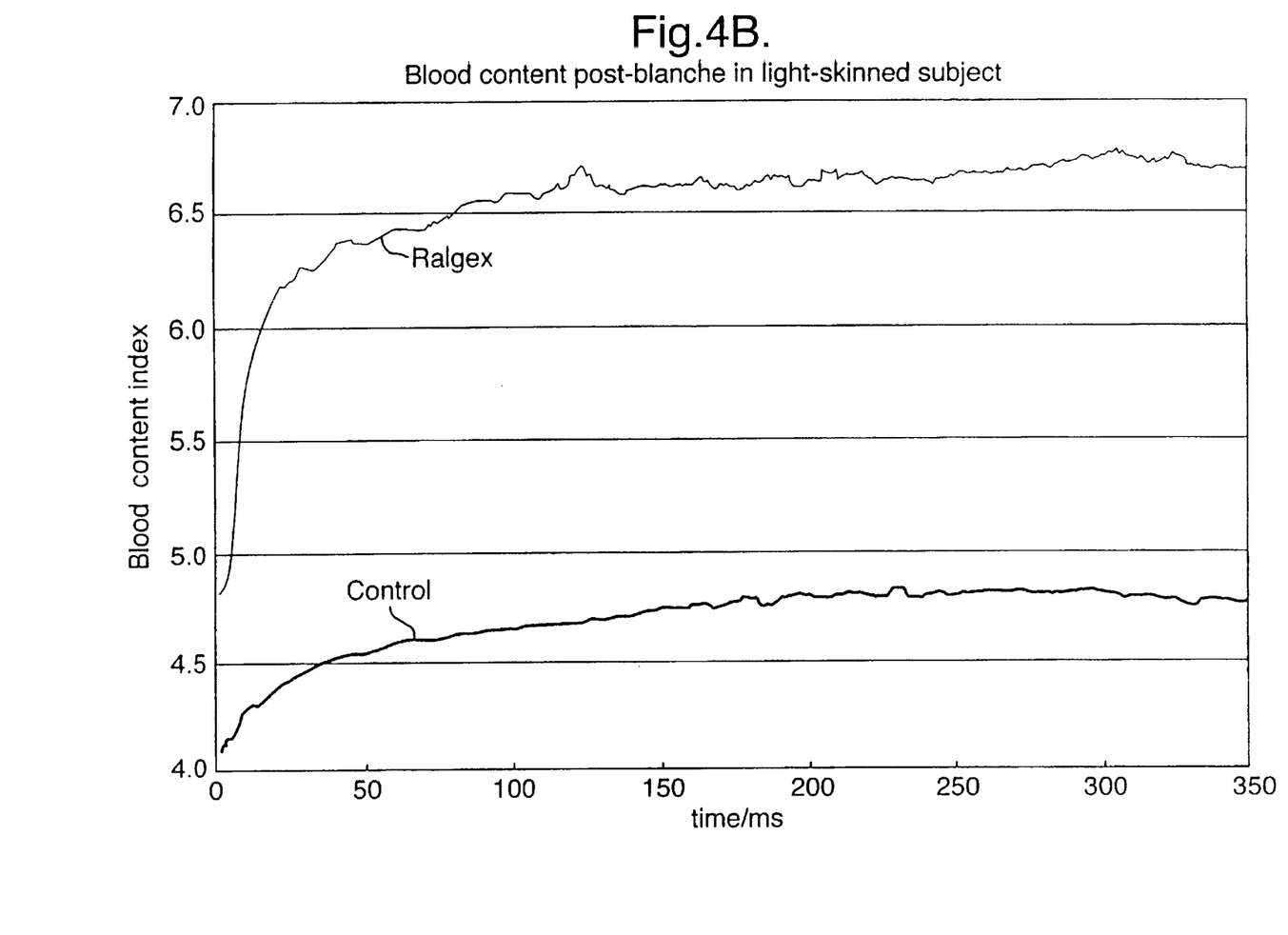

FIG. 4A shows a graph of the blood content against time of normal skin (Control) and inflamed skin (Ralgex) for a dark-skinned subject and FIG. 4 shows a graph of the blood content against time of normal skin and of inflamed skin for a light skinned subject according to the invention. As seen, the blood content is higher in the inflamed skin in both the light and the dark skinned patient.

Figure 5A:
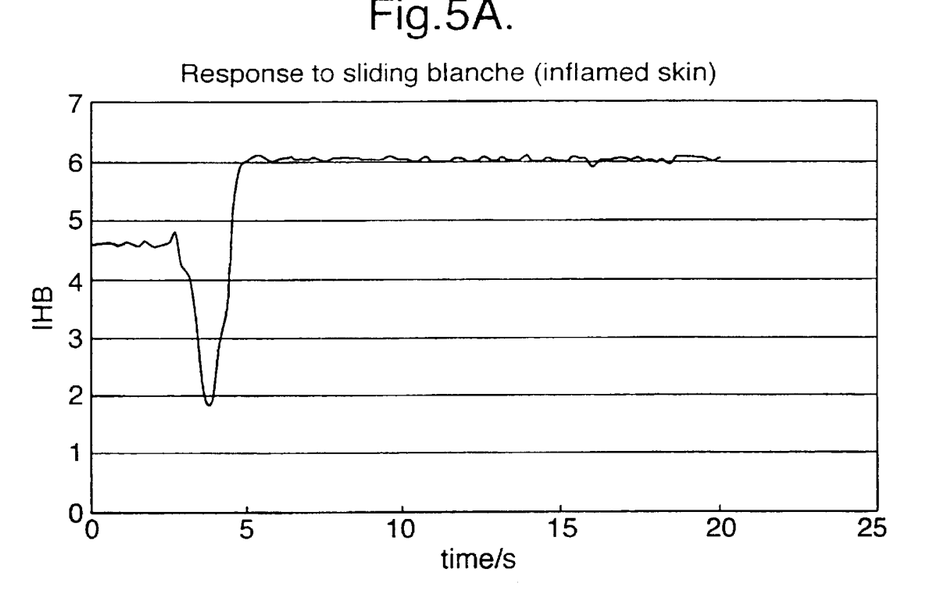
FIGS. 5A and 5B are graphs showing the response to blanching as blood content recovery rate against time.
Figure 5B:
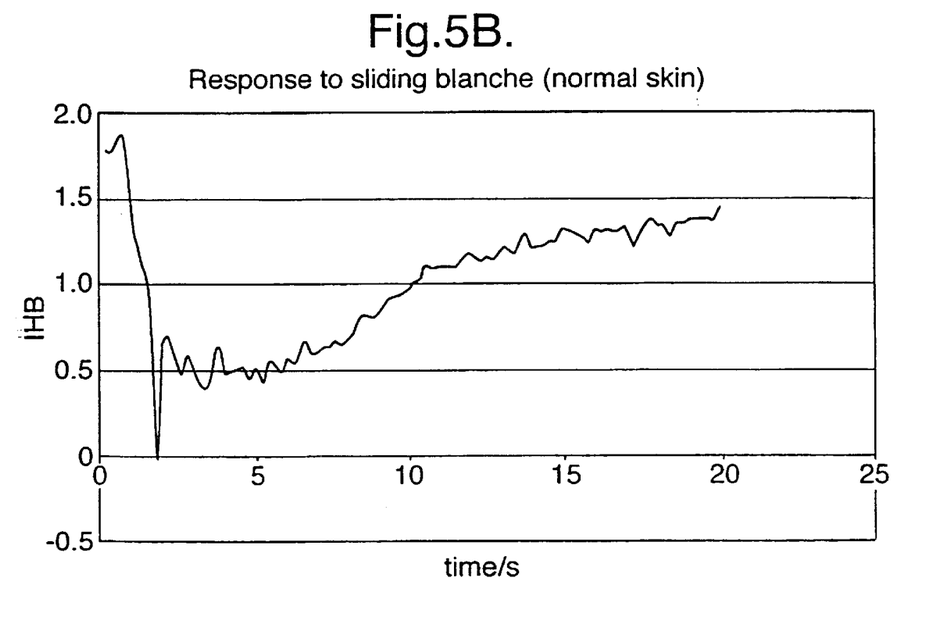

FIG. 5A is a graph of the blood content recovery rate of inflamed skin and FIG. 5B of normal skin as a response to blanching according to the invention. FIG. 5A shows that inflammatory skin conditions exhibit a fast recovery of blood content and even exceed the blood content before blanching, whereas normal skin exhibits a slow response. Hemorrhaged skin exhibits little blanching.

The points on the graphs may also be analysed for blood composition to give a better indication of the state of the blood, for example blood oxygen level, which allows identification of bruising and necrotic tissue.

The emitter/sensor (3) may continuously measure quantities as above associated with blood content before, during, and after blanching. Quantification of the blood content prior to blanching, the extent of blanching (blood content during blanching), the rate of return of blood content after blanching, and the new level of blood content after blanching, provide information required to characterise the condition of the skin. These measurements may form the basis of an 'expert system' that will make an objective diagnosis of the status of the tissue's blood circulation and accordingly may be used as a predictor of the likelihood of tissue breakdown or of further damage occurring if corrective measures are not taken. Numerical indices may be generated for recording the patient's skin characteristics.

Even though the specification describes the use of wavelengths, the use of frequencies is equally valid.

What is claimed is:

1. An apparatus for evaluating microcirculatory status or damage adjacent a tissue surface comprising:
   means for applying a mechanical stimulus to the a tissue surface;
   means for delivering light to the tissue;
   one or more sensors for detecting light recovered from the tissue; and
   processor means, connected to the sensor(s) and the delivery means, for determining the attenuation of different wavelengths of light scattered within the tissue to provide an indication of the state of microcirculation of the tissue;
   wherein the means for applying a mechanical stimulus comprises a housing having a blanching edge to apply a sliding force on the tissue surface to provide a blanching effect.

2. An apparatus as claimed in claim 1, wherein the means for applying a mechanical stimulus is powered.

3. An apparatus as claimed in claim 1, wherein the blanching edge has rotary or linear movement.

4. An apparatus as claimed in claims 3, wherein the movement of the blanching edge is at a controlled rate to give a known time interval between the blanching edge and the sensor(s).

5. An apparatus as claimed in claim 1, wherein the blanching edge is oblique relative to the direction of motion, to displace blood laterally.

6. An apparatus as claimed in claim 1, wherein the means for delivering light is located remote from the housing.

7. An apparatus as claimed in claim 1, wherein the sensor(s) is located adjacent the blanching edge within the housing for more accurate measurements.

8. An apparatus as claimed in claim 1, wherein the means for delivering light is located within the housing for a more compact diagnostic apparatus.

9. An apparatus as claimed in claim 3, wherein the rotary or linear movement of the blanching edge is relative between the blanching edge and the sensor(s).

10. An apparatus for evaluating microcirculatory status or damage adjacent a tissue surface comprising:
    means for applying a mechanical stimulus to the a tissue surface;
    means for delivering light to the tissue;
    one or more sensors for detecting light recovered from the tissue; and
    processor means, connected to the sensor(s) and the delivery means, for determining the attenuation of different wavelengths of light scattered within the tissue to provide an indication of the state of microcirculation of the tissue;
    wherein the processor means measures the level and ratio of oxygenated to deoxygenated blood in the tissue.

11. A method for evaluating microcirculatory damage adjacent to a tissue surface comprising the steps of:
    applying a mechanical stimulus to the tissue surface;
    exposing the tissue to light;
    measuring the attenuation of at least two wavelengths of the light scattered within the tissue and collected by one or more sensors, the at least two wavelengths selected based upon absorption of the light associated with a presence of blood beneath the tissue surface and absorption of the light associated with a pigmentation of the tissue, and; T
    computing as at least a partial function of said absorptions blood content against time upon removal of the application of the mechanical stimulus to indicate the state of microcirculation of the tissue.

12. A method as claimed in claim 11, wherein the application of the mechanical stimulus comprises applying a pressure.

13. A method as claimed in claim 11, wherein the blood content is indicated on a display.

14. A method as claimed in claim 11, further comprising the step of quantitatively assessing the pigmentation of the tissue.

15. An apparatus for evaluating microcirculatory status or damage adjacent a tissue surface comprising:
    means for applying a mechanical stimulus to the tissue surface, means for delivering light to the tissue:

one or more sensors for detecting light recovered from the tissue; and processor means, connected to the sensor(s) and the delivery means, for determining the attenuation of different wavelengths of light scattered within the tissue to provide an indication of the state of microcirculation of the tissue;

wherein the processor means quantitatively assesses the pigmentation of the tissue.

16. A method for evaluating microcirculatory damage adjacent to a tissue surface comprising the steps of:

applying a mechanical stimulus to the tissue surface;

exposing the tissue to light;

measuring the attenuation of different wavelengths of the light scattered within the tissue and collected by one or more sensors and;

computing blood content against time upon removal of the application of the mechanical stimulus to indicate the state of microcirculation of the tissue;

wherein applying the mechanical stimulus comprises applying a sliding force on the surface of the tissue.

17. An apparatus for evaluating microcirculatory status or damage adjacent a tissue surface comprising:

means for applying a mechanical stimulus to the tissue surface;

means for delivering electromagnetic radiation to the tissue;

one or more sensors for detecting electromagnetic radiation recovered from the tissue; and processor means, connected to the sensor(s) and the delivery means, for determining the attenuation of electromagnetic radiation scattered within the tissue to provide an indication of the state of microcirculation of the tissue;

wherein the means for applying a mechanical stimulus comprises a housing having a blanching portion to apply a sliding force on the tissue surface to provide a blanching effect.

18. An apparatus for evaluating microcirculatory status or damage adjacent a tissue surface comprising:

means for applying a mechanical stimulus to the tissue surface;

means for delivering electromagnetic radiation to the tissue, one or more sensors for detecting light recovered from the tissue; and processor means, connected to the sensor(s) and the delivery means, for determining the attenuation of at least two wavelengths of the electromagnetic radiation scattered within the tissue to provide an indication of the state of microcirculation of the tissue, the at least two wavelengths selected based upon absorption of the electromagnetic radiation associated with a presence of blood beneath the tissue surface and absorption of the electromagnetic radiation associated with a pigmentation of the tissue.

19. A method for evaluating microcirculatory damage adjacent to a tissue surface comprising the steps of:

applying a mechanical stimulus to the tissue surface:

exposing the tissue surface to electromagnetic radiation;

measuring the attenuation of at least two wavelengths of the electromagnetic radiation scattered within the tissue and collected by one or more sensors, the at least two wavelengths selected based upon absorption of the electromagnetic radiation associated with a presence of blood beneath the tissue surface and absorption of the electromagnetic radiation associated with a pigmentation of the tissue, and;

computing as at least a partial function of said absorptions blood content against time upon removal of the application of the mechanical stimulus to indicate the state of microcirculation of the tissue.

* * * * *

UNITED STATES PATENT AND TRADEMARK OFFICE
CERTIFICATE OF CORRECTION

PATENT NO.    : 6,631,288 B1
DATED         : October 7, 2003
INVENTOR(S)   : Bain et al.

It is certified that error appears in the above-identified patent and that said Letters Patent is hereby corrected as shown below:

<u>Column 5,</u>
Line 57, delete "a" following "to the".

<u>Column 6,</u>
Line 9, delete "claims" and insert -- claim -- in its place.
Line 28, delete "a" following "to the".
Line 51, delete "T" following "of the tissue, and;".

Signed and Sealed this

Eleventh Day of November, 2003

JAMES E. ROGAN
*Director of the United States Patent and Trademark Office*